United States Patent
Barham et al.

(10) Patent No.: US 7,115,800 B2
(45) Date of Patent: Oct. 3, 2006

(54) SEEDLESS WATERMELON HAVING SMALL FRUIT

(75) Inventors: Robert Barham, Gilroy, CA (US);
Warren Barham, Gilroy, CA (US);
Fred T. McCuistion, Tifton, GA (US);
Benito Juarez, Woodland, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 189 days.

(21) Appl. No.: 10/323,603

(22) Filed: Dec. 18, 2002

(65) Prior Publication Data

US 2003/0172413 A1    Sep. 11, 2003

Related U.S. Application Data

(60) Provisional application No. 60/340,276, filed on Dec. 18, 2001.

(51) Int. Cl.
| | |
|---|---|
| *A01H 5/00* | (2006.01) |
| *A01H 5/10* | (2006.01) |
| *A01H 1/00* | (2006.01) |
| *A01H 4/00* | (2006.01) |
| *C12N 15/82* | (2006.01) |

(52) U.S. Cl. .................... 800/308; 800/260; 800/298; 435/410

(58) Field of Classification Search ................ 435/413, 435/418, 421, 430, 430.1, 410; 800/260, 800/268, 269, 271, 279, 308, 266
See application file for complete search history.

(56) References Cited

U.S. PATENT DOCUMENTS 5,523,520 A * 6/1996 Hunsperger et al. ........ 800/260

OTHER PUBLICATIONS

Kihara et al. Proceedings of American Society for Horticultural Science 58: 217-230 (1951).*
Kraft et al. Theor. Appl. Genet. 101: 323-326 (2000).*
Eshed et al. Genetics 143: 1807-1817 (1996).*
Henderson et al. J. Heredity 89: 50-53 (1998).*
NeSmith et al. HortScience 36(1): 60-61 (2001).*
El-Hafez, A.A. Acta Agronomica Academiae Scientiarum Hungaricae 31(1/2): 66-70 (1982).*
Crall et al. HortScience 29(6): 707-708 (1994).*
Susin et al. Euphytica 93: 369-373 (1997).*

* cited by examiner

*Primary Examiner*—David H. Kruse
*Assistant Examiner*—Keith O. Robinson
(74) *Attorney, Agent, or Firm*—Alissa M. Eagle; David R. Marsh; Arnold & Porter LLP

(57) ABSTRACT

The present invention is a novel method which results in the production of small seedless watermelon fruit having an average fruit weight of less than 12.0 pounds. The novel method involves using small tetraploid parental lines to produce small triploid hybrid seed.

9 Claims, No Drawings

SEEDLESS WATERMELON HAVING SMALL FRUIT

CROSS REFERENCE

This application is related to and claims priority under 35 U.S.C. § 119(e) to Provisional Patent Application Ser. No. 60/340,276, filed Dec. 18, 2001, incorporated herein by reference.

BACKGROUND OF THE INVENTION

The present invention relates to a novel seedless watermelon having an average fruit weight of less than 12.0 pounds. The present invention also relates to a seedless watermelon seed, a seedless watermelon plant, seedless watermelon variety, and a seedless watermelon hybrid and to methods of producing seedless watermelon fruit.

Watermelon belongs to the family Cucurbitaceae. Watermelon is commercially grown from either seed or transplants. Citrullus is a member of the family Cucurbitaceae. The Cucurbitaceae is a family of about 90 genera and 700 to 760 species, mostly of the tropics. The family includes pumpkins, squashes, gourds, melons, cucumber, watermelon, loofah, and several weeds. A bitter-fruited form of Citrullus vulgaris appears to be the ancestor of the cultivated watermelon.

Successful watermelon production depends on attention to various cultural practices. This involves soil management practices with special attention to proper fertilization, crop establishment with appropriate spacing, weed control, the introduction of bees for pollination, and suitable pollenizers for seedless watermelon, irrigation and pest management. Watermelon fruit size and shape; rind color; thickness and toughness; seed size, color and number; and flesh color, texture, soluble solids and freedom from fruit defects are all important characteristics to be considered in selection of watermelon varieties. In addition, seedless watermelons should be free of hard seeds and have undeveloped seeds that are small and innocuous.

Watermelon crops can be established in the field from seed or from transplants. Transplanting is becoming more common because transplanting usually results in earlier crops than those that are direct seeded. Transplants are used extensively to establish seedless watermelon plantings. Diploid and triploid watermelon crops can be established easily with high quality transplants. Transplanting helps achieve rapid, complete plant stands, especially where seed costs make direct-seeding risky and expensive, as is the case with seedless watermelons. Most watermelon growers purchase plants from plant growing experts who may arrange for transport to the field location.

For triploid seedless watermelon production, fruit set and enlargement is dependent upon growth regulators from the pollen grains and from embryos in developing seeds within the fruit. Inadequate pollination results in triploid watermelon fruit that are triangular in shape and of poor quality. Inadequate pollination may increase the incidence of hollowheart. Triploid watermelon flowers do not produce sufficient viable pollen to induce fruit set and development. Therefore, pollen from a normal diploid seeded watermelon variety must be provided. Planting the diploid pollenizer variety in the outside row of the field and then every third row is recommended. As an alternative, the pollenizer variety has been planted every third plant in each row but this makes harvesting of the triploid fruit difficult because mixed diploid and triploid fruit must be separated. This also makes planting difficult because blanks must be left where the diploid should go. Maintaining the rotation of three triploid to one diploid is not easily accomplished.

Currently, it is important to use a diploid pollenizer variety that is marketable because between one-quarter to one-half of all watermelons produced in the field will be of this variety. The rind pattern and/or shape of the seeded pollenizer fruit should be distinguished easily from that of the triploid fruit to reduce confusion at harvest.

It is important that pollen from the diploid pollenizer variety is available when female blossoms on the triploid plants are open and ready for pollination. If planted too early, the diploid variety can set fruit and stop producing male blossoms while the triploid variety is still producing many female blossoms. If planted too late, the triploid will be ready to set fruit but not enough pollen will be ready to provide fruit set.

Watermelon plants develop several vigorous and far-reaching vines, thus requiring large amounts of space for optimum growth and fruit development. Watermelons have been seeded with about two to about four feet between plants in rows about six to about 15 feet apart. This wide spacing requires larger field sizes. Also, the wide spacing provided less interplant competition for water. Cultural practices such as irrigation and polyethylene mulch have led to the use of higher plant populations. Row spacing of 6–8 feet apart and plant spacing of 2–4 feet are common. Often, with close plant spacing, the individual plant sets fewer fruits, which still reach normal size.

Watermelon plants usually have separate male and female flowers but sometimes produce perfect flowers. To achieve fruit set, pollen from the male flower must be transferred to a female flower on that plant or another plant in the field. This pollen transfer is accomplished by several naturally occurring insects, but most effectively by the honeybee. Poor or ineffective pollination of watermelons results in bottle-neck fruits of long-fruited watermelon varieties. In round-fruited varieties, poorly pollinated fruits can be flat-sided or misshapen.

Watermelon has small flowers. Flowering begins about 8 weeks after seeding. Flowers of watermelon are staminate (male), perfect (hermaphroditic), or pistillate (female), usually borne in that order on the plant as it grows. Monecious types are most common, but there are andromonoecious (staminate and perfect) types, mainly the older varieties or accessions collected from the wild. In many varieties, the pistillate or perfect flowers are borne at every seventh node, with staminate flowers at the intervening nodes. The flower ratio of typical watermelon varieties is 7 staminate to 1 pistillate, but the ratio ranges from 4:1 to 15:1.

Watermelon is the only economically important cucurbit with pinnatifid (lobed) leaves; all of the other species have whole (nonlobed) leaves. The leaves are pinnately divided into three or four pairs of lobes, except for an entire-leaf (nonlobed) gene mutant controlled by the nl (nonlobed) gene. Watermelon growth habit is a trailing vine. The stems are thin, hairy, angular, grooved, and have branched tendrils at each node. The stems are highly branched and up to 30 feet long, although there are dwarf types (dw-1 and dw-2 genes) with shorter, less-branched stems. Roots are extensive but shallow, with a taproot and many lateral roots.

Vine length of watermelon varies from dwarf to long. For example, 'Charleston Gray' and 'Jubilee', large-fruited varieties, have vines up to 30 feet long. Short or medium length vines are well suited to varieties with small or medium sized fruit. For example, 'Sugar Baby', 'New Hampshire Midget', and 'Petite Sweet' are short vined, having vine lengths of between about six to about 12 feet and 'Crimson Sweet' has intermediate vine length.

Dwarf mutants have been discovered in watermelon. Two genes cause dwarfing when they are in homozygous recessive condition: dw-1 and dw-2. 'Kengarden' has the genotype dw-1 dw-2. Another gene mutant (Japanese Dwarf, dw-2 dw-2) has increased branching from the crown.

Fruit size is an important consideration in a breeding program since there are different market requirements for particular groups of shippers and consumers. The general categories are: icebox (<12 lb), small, sometimes called pee-wee (12–18 lb), medium (18–24 lb), large (24–32 lb), and giant (>32 lb). Fruit size is inherited in polygenic fashion, with an estimated 25 genes involved. Shippers in the United States work with particular weight categories, such as 18–24 lb for seeded and 14–18 lb for seedless. Researchers have developed three diploid seeded varieties with small fruit: New Hampshire Midget, Minilee and Mickylee. (Barnes, et al., Australian Journal of Experimental Agriculture. 1994. 34(5):673–679.)

The commercially available seedless watermelons have a round to round/oval to blocky shape with an average weight between 15–20 pounds. The length/width ratio (L/W ratio) for these commercial hybrids ranges from 1.2 (10×8.5 inches) to 1.7 (11.5×7 inches). There may be exceptional circumstances where the weight can go up to 32 pounds in the larger extreme; and there may be also cases where fruits weigh as little as 12–15 pounds in the smaller extreme. However the standard weight in the seedless watermelon trade in the U.S. is that of 15–20 pounds. These ranges of measurements and ratios apply for hybrid seedless watermelons grown in commercial fields and under conventional spacing between the rows and within the rows.

Seedless triploid varieties are produced by crossing a tetraploid (2n=4x=44 chromosomes) inbred line as the female parent with a diploid (2n=2x=22) inbred line as the male parent of the hybrid. The reciprocal cross (diploid female parent) does not produce seeds. The resulting hybrid is a triploid (2n=3x=33). Triploid plants have three sets of chromosomes, and three sets cannot be divided evenly during meiosis. This results in nonfunctional female and male gametes although the flowers appear normal. Since the triploid hybrid is female sterile, the fruit induced by pollination tend to be seedless. Unfortunately, the triploid has no viable pollen, so it is necessary to plant a diploid variety in the production field to provide the pollen that stimulates fruit to form. Usually, one third of the plants in the field are diploid and two thirds are triploid, although production has been observed with as little as 20% diploids. Varieties should be chosen that could be distinguished easily so the seeded diploid fruit can be separated from the seedless triploid fruit for harvesting and marketing.

Most of the tetraploid lines being used by the seed industry have gray rind so that, when crossed with a diploid line with striped rind, it will be easy to separate self-pollinated progeny (which will be seeded fruit from the female parent line) from cross-pollinated progeny (which will be seedless fruit from the triploid hybrid). The grower may discard the gray fruit so they are not marketed as seedless watermelons by mistake. For example, if there is 4% of the fruit from the inbred parent then 4% of total fruits will be unmarketable and reduces marketable yield.

A smaller fruited seedless watermelon, if available, would be desirable for certain segments of the consumer market.

SUMMARY OF THE INVENTION

The present invention relates to a novel seedless watermelon having an average fruit weight of less than 12.0 pounds. The present invention also relates to a seedless watermelon seed, a seedless watermelon plant, seedless watermelon variety, and a seedless watermelon hybrid.

The present invention also relates to a novel method of producing small fruited triploid watermelon seed by using small tetraploid and small diploid parental lines which are either transplanted or seeded into the row. The present invention also relates to a seedless watermelon plant, and a seedless watermelon hybrid which produces small seedless fruits having an average fruit weight of less than 12.0 pounds. Specifically, the claimed invention involves the following steps to produce seedless watermelon fruit:

1) planting triploid plants and diploid plants in one or more rows;
2) allowing said plants to mature and develop fruit; and
3) harvesting said fruit;

wherein said fruit has an average fruit weight of less than 12.0 pounds.

DEFINITIONS

In the description and tables which follow, a number of terms are used. In order to provide a clear and consistent understanding of the specification and claims, including the scope to be given such terms, the following definitions are provided:

Average fruit weight. As used herein, "average fruit weight" means the average weight in pounds of all fruits harvested from one or more watermelon plants of a specific genotype.

Average fruit length. As used herein, "average fruit length" means the average length of all fruits harvested from one or more plants of a specific genotype.

Average fruit width. As used herein, "average fruit width" means the average width of all fruits harvested from one or more plants of a specific genotype.

Average length to width ratio (L/W Ratio). As used herein, "length to width ratio (L/W ratio) means the average length to width ratio from all fruits harvested from one or more plants of a specific genotype.

Average internode length. As used herein the term "average internode length" means the average length of the internodes of a plant genotype measured in inches.

Lobed leaf. As used herein the term "lobed leaf" means a leaf having two or more lobes.

Nonlobed leaf. As used herein the term "nonlobed leaf" means a leaf that is not lobed.

Yield. As used herein, the term "yield" means the total weight in pounds of all watermelon fruit harvested per acre.

Plant. As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seed, leaves, stems, rind, flesh and the like.

Quantitative Trait Loci (QTL). As used herein, the term "quantitative trait loci (QTL)" refer to genetic loci that control to some degree numerically representable traits that are usually continuously distributed.

Regeneration. Regeneration refers to the development of a plant from tissue culture.

Seedless. As used herein, the term "seedless" means a watermelon fruit in which the embryo development is aborted and the seed development process has stopped before producing a mature viable seed. Seedless fruit may contain traces of the developing seed and occasionally a seed coat may form and become hard and have the appearance of a seed.

Plant diameter. As used herein, the term "plant diameter" means the average length of plant measurements in inches.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Vine length. As used herein, the term "vine length" is the length of the runners (vines) and is measured in inches.

Average length of longest runner. As used herein, the term "average length of longest runner" means the average length of the longest runner of the watermelon plant in inches.

Triploid plants. As used herein, "triploid plants" means plants or transplants derived from planting triploid seeds or from micro propagation.

Diploid plants. As used herein, "diploid plants" means plants or transplants derived from planting diploid seeds or from micro propagation.

Explosive rind. As used herein, "explosive rind" in watermelon is a trait where the rind is tender and can burst open when cut with a knife. The rind can also explode before the watermelon fruit reaches physiological maturity and results in unmarketable fruit.

Thick rind. As used herein, "thick rind" is inherited in a polygenic fashion (controlled by more than one gene). Thick rind is proportional with the overall fruit diameter (fruit size). A rind thickness of ¾" is acceptable for a 16 pound watermelon; but for a 10 pound watermelon the rind should be of no more than ¼" to be marketable.

Hollowheart: As used herein "hollowheart" is the characteristic of separation of tissue within the endocarp which can be caused by rapid fruit growth and weak tissue. The presence of Hollowheart (or one variant which is placental detachment) is affected by environment, but can also be selected against in the development of inbred lines. The genetic control of this undesirable trait is not understood.

Rind pattern: As used herein, the "rind pattern" is the coloration of the rind in watermelons which can vary from light green, often termed gray, to medium green to very dark green which appears to be almost black. In addition, the rind may have stripes of various designs which are typical of a variety or type. Therefore the terms 'tiger stripe', 'mottle stripe', 'dark mottle stripe', etc. are used to identify various patterns.

DETAILED DESCRIPTION OF THE INVENTION

The present invention relates to a novel method of producing small triploid watermelon fruit which involves the use of both small fruited tetraploid and small fruited diploid parental lines. The present invention also relates to a watermelon plant, a watermelon inbred and a watermelon hybrid which can be used to produce fruits having an average fruit weight of less than 12.0 pounds.

In the present invention, small seedless triploid seeds and plants are produced by crossing a small tetraploid (2n=4x=44 chromosomes) inbred line as the female parent with a small diploid (2n=2x=22) inbred line as the male parent of the hybrid. The reciprocal cross (diploid female parent) does not produce seeds. The resulting hybrid is a triploid (2n=3x=33). Triploid plants have three sets of chromosomes, and three sets cannot be divided evenly during meiosis. This results in nonfunctional female and male gametes although the flowers appear normal. Since the triploid hybrid is female sterile, the fruit induced by pollination tend to be seedless. Unfortunately, the triploid has no viable pollen, so it is necessary to plant a diploid variety in the production field to provide the pollen that stimulates fruit to form. Usually, one third of the plants in the field are diploid and two thirds are triploid, although production has been observed with as little as 20% diploids. Varieties should be chosen that could be distinguished easily so the seeded diploid fruit can be separated from the seedless triploid fruit for harvesting and marketing.

The present invention is a novel method which crosses a small-fruited tetraploid as the seed parent and a small-fruited diploid as the male parent to produce triploid seed and plants of a small fruited seedless watermelon having an average fruit weight of less than 12.0 pounds. In the present invention, the tetraploid and diploid parental lines used to create small fruited triploids have been selected and bred to have small fruit and small seeds which produce small seed traces or pips in the triploid hybrid. The fruits produced by growing the triploid hybrid that results from this pollination and method are genetically small and are seedless. This novel method allows the triploid hybrid to produce smaller than conventional fruit sizes that can be grown using standard cultural practices and have the advantage to the consumer of being a "one-serving" product. The use of this novel small fruited seedless watermelon also allows easier harvesting of the triploid fruits produced, since the weight is less than the fruits of currently used seedless hybrids.

In another embodiment of the present invention, the small seedless watermelon fruits have a length of between about 6 to about 11 inches.

In another embodiment of the present invention the small seedless watermelon fruits have a width of between about 5 inches to about 9 inches.

In another embodiment of the present invention, the small seedless watermelon fruits have a length to width ratio (L/W ratio) of between about 1. to about 1.9.

The established plants in a field of the present invention can be developed from the following methods: 1) planting seeds or any portions of seed; 2) primed or coated seed, or any portions of the seed; 3) plants, or portions thereof, derived from tissue culture or cell culture; 4) cuttings; and 5) planting transplants into the field.

The triploid and diploid seeds of the present invention can be mixed prior to planting and then sowed or the triploid seed can first be planted, followed by planting the diploid seed or vice versa, depending on expected pollination dates.

Previously, researchers have developed and released three diploid varieties with small fruit: "New Hampshire Midget" (NHM), "Minilee" (MN), and "Mickylee" (MK). The varieties New Hampshire Midget, Minilee and Mickylee all are diploid watermelons with seeds and have a diploid chromosome number (2n=2x=22). To make a triploid (seedless) watermelon hybrid one of the lines (that will become the seed parent or female parent) will need to have the chromosome number doubled (2n=4x=44 chromosomes) to produce tetraploids.

When these three diploid lines (NHM, MN, MK) are doubled this results in a number of problems which prevent the production of triploid seedless watermelon. One problem is the presence of hard seed coats in the triploid hybrids resulting from these tetraploids. The lines MN and MK when doubled to become tetraploid are highly sterile (particularly female sterile) and produce from zero to only a few seeds per fruit. This results in a problem for seed increase of the line and also is a big problem at the time of making the triploid hybrid since often no seeds are produced in the tetraploid. Besides the problem of high sterility when in the tetraploid phase and the problems with hard seed coat in the triploids, additional problems include: hollow heart, placental detachment from the rest of the flesh, thick rind, and in the case of NHM the problem of explosive rind. Explosive rind is a trait that causes the fruit to split open before (or at the time) the fruit reaches maturity. This ruins the production of the commercial watermelon fruit. Another disadvantage with the MN, MK and NHM diploid lines is that they have a light green color rind pattern (so called "gray rind"). People prefer to consume watermelons with different rind patterns than gray rind (i.e., dark green, mottle striped, etc.).

Hard seed coats, thick rind, explosive rind and hollow heart characteristics in the fruit make the product unsatisfactory for commercial marketing purposes. The diploid versions of MN, MK and NHM are also unattractive to the consumer because they are full of seeds.

The present invention resulted in seedless watermelon hybrids, and eliminated the negative traits associated with these previous lines. Unexpectedly the lines of the present invention listed in Tables 1–3 do not have the problems of: 1) being highly female sterile; 2) producing hard seed coats in the triploid (seedless) fruit; 3) hollow heart, 4) thick rind, and 5) explosive rind.

Also, unexpectedly small seedless watermelon fruit of less than 12 pounds were produced where the seed parents (tetraploid) do not have high sterility. It was also unexpected that a seedless watermelon fruit of less than 12 pounds can be produced without the negative traits of 1) explosive rind, 2) hollow heart, and 3) a gray rind pattern.

EXAMPLES

The present invention is further detailed in the following Examples, which are offered by way of illustration and are not intended to limit the invention in any manner. Standard techniques well known in the art or the techniques specifically described are utilized.

Example 1

Tetraploid and Diploid Parental Lines

Numerous tetraploid parental lines of the present invention have been developed and are listed in Table 1. Also listed in Table 1 are numerous diploid parental lines of the present invention with small fruits and small seed size which can be used in the method of the present invention. There are approximately 31–35 diploid lines that have been crossed with other small tetraploid plants of the present invention to produce triploid hybrids which then can be grown to produce small seedless fruit.

TABLE 1

Diploid and Tetraploid Parental Lines

| Number/ID | Rind Pattern | Flesh Color | Fruit Shape | Ploidy |
|---|---|---|---|---|
| 1671 | Gray | Red | Round/Oval | Tetraploid |
| 1674 | Gray | Red | Round | Tetraploid |
| 1696 | Gray | Red | Oval | Tetraploid |
| 1670 | Gray | Red | Round | Tetraploid |
| 1675 | Gray | Red | Round | Tetraploid |
| 1672 | Gray | Red | Round | Tetraploid |
| 1885 | Dark green | Red | Round | Tetraploid |
| 2526 | Gray | Red | Oval/Blocky | Diploid |
| 2321 | Mottle stripe | Red | Blocky | Diploid |
| 2201 | Tiger Stripe | Red | Round | Diploid |
| 2142-1 | Dark Green | Red | Round/Oval | Diploid |
| 2552-1 | Mottle stripe | Red | Oval | Diploid |
| 2841 | Tiger stripe | Red | Round/Oval | Diploid |
| 3128 | Dark green | Red | Round | Diploid |
| 02-6003 | Dark Mottle Stripe | Red/orange | Blocky | Tetraploid |
| 02-6107 | Dark Mottle Stripe | Red | Blocky | Tetraploid |
| 02-6154 | Mottle Stripe | Red | Round | Tetraploid |
| 02-6210 | Mottle Stripe | Red | Round | Tetraploid |
| 02-6278 | Dark Mottle Stripe | Red | Round | Tetraploid |
| 02-6279 | Dark Mottle Stripe | Red | Round | Tetraploid |
| 02-6339 | Mottle Stripe | Red | Round | Tetraploid |
| 02-6495 | Dark Green/Black | Red/orange | Round | Tetraploid |
| 02-6605 | Gray | Red | Oval/blocky | Tetraploid |
| 02-6614 | Gray | Red | Blocky | Tetraploid |
| 02-6696 | Gray | Red | Round | Tetraploid |
| 02-6711 | Gray | Red | Round | Tetraploid |
| 02-6712 | Gray | Red | Round | Tetraploid |
| 02-6713 | Gray | Red | Round | Tetraploid |
| 02-6716 | Gray | Red | Round | Tetraploid |
| 02-6757 | Gray | Red | Round | Tetraploid |
| 110-4700 | Gray | Red | Round/oval | Tetraploid |
| 02F1862-1 | Tiger Stripe | Yellow | Round | Tetraploid |
| 02F1862-2 | Tiger Stripe | Yellow | Round | Tetraploid |
| 02F1862-3 | Gray | Yellow | Round | Tetraploid |
| 02F1811-1 | Dark Green | Red | Round | Tetraploid |
| 02F2427-1 | Dark Mottle Stripe | Red | Round | Tetraploid |
| 02F2434-1 | Dark Green | Red | Round | Tetraploid |
| 02F1616-1 | Tiger Stripe | Yellow | Round | Diploid |
| 02F1632-1 | Gray | Yellow | Round | Diploid |
| 02F1633-1 | Gray | Yellow | Round | Diploid |
| 02-5607 | Gray | Red | Blocky | Diploid |
| 02-5612 | Gray | Red | Round/oval | Diploid |
| 02-5618 | Dark Green | Red | Round/oval | Diploid |
| 02-5624 | Dark Green | Red | Round/oval | Diploid |
| 02-5625 | Tiger Stripe | Red | Round/oval | Diploid |
| 02-5626 | Tiger Stripe | Red | Round | Diploid |
| 02-5628 | Dark Green | Red | Round | Diploid |
| 02-5629 | Dark Green | Red | Round/oval | Diploid |
| 02-5631 | Mottle Stripe | Red | Round/oval | Diploid |
| 02-5632 | Mottle Stripe | Red | Round/oval | Diploid |
| 02-5640 | Mottle Stripe | Red | Round | Diploid |
| 02-5661 | Mottle Stripe | Red | Elongated | Diploid |
| 02-5668 | Mottle Stripe | Red | Elongated | Diploid |
| 02-5693 | Gray | Red | Elongated | Diploid |
| 02-5695 | Gray | Red | Blocky | Diploid |
| 02-5758 | Dark Green | Red | Blocky | Diploid |
| 02-5813 | Mottle Stripe | Red | Round | Diploid |
| 02-5827 | Mottle Stripe | Red | Round | Diploid |
| 02-5853 | Mottle Stripe | Red | Round/oval | Diploid |
| 02-5861 | Mottle Stripe | Red | Round/oval | Diploid |
| 110-3128 | Dark Green | Red | Round/oval | Diploid |

Example 2

Seedless Watermelon with Small Fruit '01-1703'

The triploid hybrid plant '01-1703' produces a small fruited seedless watermelon with an average fruit weight of between 8.0 and 9.0 pounds. This triploid of the present invention results from crossing the small tetraploid line '1671' with the small diploid line '2201'. This smaller size of seedless watermelon fruit has not been commercially available from current commercial seedless production. The small fruited watermelons currently commercially available to the grower all have a diploid genetic background and therefore produce only seeded fruit. Another unique characteristic of hybrid '01-1703' is the firmer than normal flesh and a very reduced size of seed traces or pips.

| | |
|---|---|
| Vine type: | Vine |
| Total vine length: | 400 cm |
| Internode length: | 11 cm |
| Maturity: | Mid-season- ~85 days |
| Similar to: | Petite Sweet |
| Leaf type: | Lobed |
| Distance crown to fruit: | 216 cm |
| Fruit weight: | 8–9 lbs |
| Fruit shape: | Round |
| Fruit size (cm) | 18 × 18 |
| Rind thickness (cm) | 2.5 at stem end; 2.0 mid fruit; 1.0 at blossom end |
| Flesh color: | Red |
| Texture: | Firm and crisp |
| Seed traces size: | 6 mm × 4 mm |
| Blossom scar diameter (cm) | 1.2 |
| Brix: | 11.20% |
| Stripe: | Like Crimson Sweet |
| Number of main runners: | 4 |

Example 3

Seedless Watermelon with Small Fruit '01-1714'

The triploid hybrid '01-1714' of the present invention produces small fruited seedless watermelon having an average fruit weight of less than 10 pounds. Seed of this hybrid is produced by crossing the tetraploid line '1671' with the diploid line '2142'. This hybrid possesses a medium to medium-dark green rind which is the result of crossing a gray tetraploid to a dark green diploid. Currently, there are no commercially sold seedless hybrids which have smaller fruit size, with small seed traces, and a very firm flesh.

| | |
|---|---|
| Vine type: | Vine |
| Total vine length: | 490 cm |
| Internode length: | 11 cm |
| Maturity: | Mid-season- ~85 days |
| Similar to: | Minilee with shadow rind pattern |
| Leaf type: | Lobed |
| Distance crown to fruit: | 190 cm |
| Fruit weight: | 8–9 lbs |
| Fruit shape: | Round/Oval |
| Fruit size (cm) | 21 × 17.5 |
| Rind thickness (cm) | 2.0 at stem end; 1.7 mid fruit; 1.0 at blossom end |
| Flesh color: | Red to red/orange |
| Texture: | Firm and crisp |
| Seed traces size: | 5 mm × 3 mm |
| Blossom scar diameter (cm) | 1.1 |
| Brix: | 12.80% |
| Stripe: | Shadow type (DMS on DG background) |
| Number of main runners: | 3 |

Example 4

Seedless Watermelon with Small Fruit '02-8518'

This hybrid of the present invention produces a small seedless fruit size with an average fruit weight of about 9.0 pounds. Hybrid '02-8518' seed is produced by crossing the small tetraploid line '1885' with the small diploid line '3128'. The seeded hybrids of the Sugar Baby type are known for their softer than desired flesh. The fruit produced from seedless hybrid '02-8518' of the present invention have a very firm flesh in addition to very small seed traces and a higher fruit count. The small fruited diploid parental line used in this cross is very productive and contributes to the higher fruit count per plant.

| | |
|---|---|
| Vine type: | Vine |
| Total vine length: | 320 cm |
| Internode length: | 8 cm |
| Maturity: | Early Mid-season- ~80 days |
| Similar to: | Sugar Baby |
| Leaf type: | Lobed |
| Distance crown to fruit: | 162 cm |
| Fruit weight: | 9 lbs |
| Fruit shape: | Round |
| Fruit size (cm) | 20 × 18.5 |
| Rind thickness (cm) | 2.0 at stem end; 1.2 mid fruit; 1.3 at blossom end |
| Flesh color: | Red to red/orange |
| Texture: | Medium firm |
| Seed traces size: | 7 mm × 3 mm |
| Blossom scar diameter (cm) | 1 |
| Brix: | 13.40% |
| Stripe: | Black/dark green, no stripe |
| Number of main runners: | 4 |

Example 5

PS1100-1714 Harvested Boxes of Watermelon Fruits

The data in Table 2 shows the number of packed fruits. Fruits that were considered of good marketable quality and of the targeted size. Planting date of the data is Jun. 3 to Jun. 9, 2002. Total number of plants is approximately 1,800. Row distance is 60 inches and plant distance in rows is 24 inches.

TABLE 2

Seedless Small Miniwatermelon PS1100–1714
Harvested Boxes per Period

| | Fruit Size Category | | | | |
|---|---|---|---|---|---|
| Pick | 5" | 6" | 8" | # Boxes | Date |
| 1st | 36 | 31 | 1 | 68 | Aug. 01, 2002 |
| 2nd | 41 | 49 | 6 | 96 | Aug. 05, 2002 |
| 3rd | 4 | 4 | 4 | 12 | Aug. 07, 2002 |
| 4th | 27 | 29 | 7 | 63 | Aug. 09, 2002 |
| 5th | 27 | 71 | 9 | 107 | Aug. 13, 2002 |
| 6th | 1 | 4 | 4 | 9 | Aug. 16, 2002 |
| 7th | 24 | 43 | 3 | 70 | Aug. 19, 2002 |
| 8th | 4 | 14 | 9 | 27 | Aug. 21, 2002 |
| Total # Boxes | 164 | 245 | 43 | 452 | |
| Total # Fruits | 820 | 1470 | 344 | 2634 | |

Example 6

Small Seedless Triploid Hybrids Produced

Table 3 shows additional small seedless triploid hybrids that were produced in Summer 2002 in Gilroy, Calif. and were grown in Colina, Mexico in Fall 2002.

TABLE 3

Additional Examples of Seedless (triploid) Hybrids with small fruit

| Number/ID | Female Parent | Male Parent | Ploidy |
| --- | --- | --- | --- |
| 5331 | 110-1005 | 02-5612 | Triploid |
| 5332 | CB662-1 | 02-5618 | Triploid |
| 5333 | CB663-1 | 110-3128 | Triploid |
| 5334 | CB663-1 | 02-5695 | Triploid |
| 5335 | 110-1005 | 01-3683 | Triploid |
| 5336 | 110-1005 | 02-5640 | Triploid |
| 5337 | 110-1005 | 02-5853 | Triploid |
| 5338 | 110-4700 | 02-5625 | Triploid |
| 5339 | 110-4700 | 02-5626 | Triploid |
| 5340 | 110-4700 | 02-5631 | Triploid |
| 5341 | 110-4700 | 02-5632 | Triploid |
| 5342 | 110-4700 | 02-5668 | Triploid |
| 5343 | 110-4700 | 02-5827 | Triploid |
| 5344 | 110-4700 | 02-5861 | Triploid |
| 5345 | 02-6003 | 02-5607 | Triploid |
| 5346 | 02-6003 | 02-5861 | Triploid |
| 5347 | 02-6107 | 02-5640 | Triploid |
| 5348 | 02-6154 | 02-5640 | Triploid |
| 5349 | 02-6210 | 02-5640 | Triploid |
| 5350 | 02-6278 | 02-5625 | Triploid |
| 5351 | 02-6278 | 02-5668 | Triploid |
| 5352 | 02-6278 | 02-5758 | Triploid |
| 5353 | 02-6278 | 02-5827 | Triploid |
| 5354 | 02-6279 | 02-5626 | Triploid |
| 5355 | 02-6279 | 02-5640 | Triploid |
| 5356 | 02-6279 | 02-5861 | Triploid |
| 5357 | 02-6339 | 02-5640 | Triploid |
| 5358 | 02-6495 | 110-3128 | Triploid |
| 5359 | 02-6495 | 01-3689 | Triploid |
| 5360 | 02-6495 | 02-5607 | Triploid |
| 5361 | 02-6495 | 02-5618 | Triploid |
| 5362 | 02-6495 | 02-5626 | Triploid |
| 5363 | 02-6495 | 02-5629 | Triploid |
| 5364 | 02-6495 | 02-5668 | Triploid |
| 5365 | 02-6495 | 02-5693 | Triploid |
| 5366 | 02-6495 | 02-5758 | Triploid |
| 5367 | 02-6495 | 02-5861 | Triploid |
| 5368 | 02-6605 | 110-3128 | Triploid |
| 5369 | 02-6614 | 110-3128 | Triploid |
| 5370 | 02-6696 | 110-3128 | Triploid |
| 5371 | 02-6711 | 02-5624 | Triploid |
| 5372 | 02-6711 | 02-5661 | Triploid |
| 5373 | 02-6711 | 02-5668 | Triploid |
| 5374 | 02-6711 | 02-5813 | Triploid |
| 5375 | 02-6712 | 02-5628 | Triploid |
| 5376 | 02-6713 | 02-5607 | Triploid |
| 5377 | 02-6713 | 02-5612 | Triploid |
| 5378 | 02-6713 | 02-5632 | Triploid |
| 5379 | 02-6716 | 02-5632 | Triploid |
| 5380 | 02-6716 | 02-5853 | Triploid |
| 5381 | 02-6757 | 110-3128 | Triploid |
| 5382 | 02-6711 | 02-5625 | Triploid |

When the term inbred watermelon plant is used in the context of the present invention, this also includes any transgenes and single gene conversions of that inbred. The term single gene converted plant as used herein refers to those watermelon plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental watermelon plants for that inbred. The parental watermelon plant which contributes the gene for the desired characteristic is termed the nonrecurrent or donor parent. This terminology refers to the fact that the nonrecurrent parent is used one time in the backcross protocol and therefore does not recur. In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

A further aspect of the invention relates to tissue culture of watermelon plants designated '1671'. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, leaves, roots, root tips, anthers, and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels or anthers, has been used to produce regenerated plants. (See U.S. Pat. Nos. 5,445,961; 5,322, 789; 5,948,957 and 5,969,212, the disclosures of which are incorporated herein by reference).

Deposit Information

Watermelon seeds of '1671' have been placed on deposit with the American Type Culture Collection (ATCC), 10801 University Blvd., Manassas, Va. 2110, under Deposit Accession Number PTA-4858 on Dec. 13, 2002.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A seed of tetraploid watermelon line designated '1671', a sample of said seed having been deposited under ATCC Accession No. PTA-4858.

2. A watermelon plant, or a part thereof, produced by growing the seed of claim 1.

3. Pollen of the plant of claim 2.

4. An ovule of the plant of claim 2.

5. A tissue culture of regenerable cells or protoplasts produced from a watermelon plant of line '1671' wherein the tissue culture regenerates plants having all of the morphological and physiological characteristics of watermelon line '1671' a sample of seed having been deposited under ATCC Accession No. PTA-4858.

6. The tissue culture according to claim 5, the cells or protoplasts being produced from a tissue selected from the group consisting of leaves, pollen, embryos, roots, flowers and rind.

7. A watermelon plant regenerated from the tissue culture of claim 5, having all the morphological and physiological characteristics of watermelon line '1671'.

8. A method for producing a hybrid watermelon seed comprising crossing a first parent watermelon plant with a second parent watermelon plant and harvesting the resultant hybrid watermelon seed, wherein said first parent watermelon plant is the watermelon plant of claim 2, and wherein said second watermelon plant is a diploid watermelon plant.

9. The watermelon plant, or a part thereof, of claim 2, wherein the plant or part thereof has been transformed so that its genetic material contains one or more transgenes operably linked to one or more regulatory elements, and wherein the transgene confers a characteristic selected from the group consisting of herbicide resistance, insect resistance, and resistance to bacterial, fungal, or viral disease.

* * * * *